Figure 1:
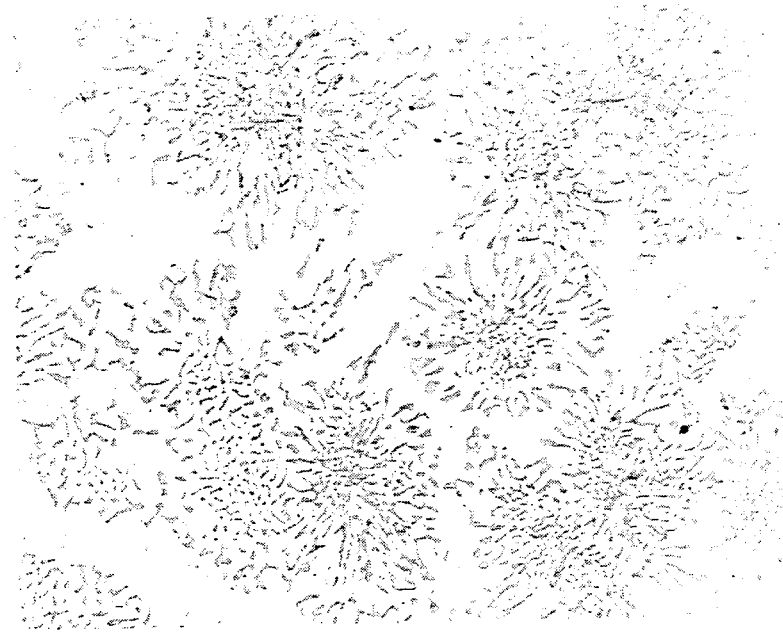

United States Patent [19]

Barlow et al.

[11] Patent Number: 5,019,178

[45] Date of Patent: May 28, 1991

[54] ALUMINUM-SILICON ALLOY ARTICLE AND METHOD FOR ITS PRODUCTION

[75] Inventors: John Barlow, Walsall; Philip H. Evans, Lichfield; Nicholas H. Frank, Wensley; Hamish D. Wilson, Grassmore, all of England

[73] Assignee: GKN Technology Limited, Wolverhampton, England

[21] Appl. No.: 469,546

[22] PCT Filed: Oct. 17, 1988

[86] PCT No.: PCT/GB88/00875

§ 371 Date: Mar. 21, 1990

§ 102(e) Date: Mar. 21, 1990

[87] PCT Pub. No.: WO89/03895

PCT Pub. Date: May 5, 1989

[30] Foreign Application Priority Data

Oct. 19, 1987 [GB] United Kingdom ............... 8724469

[51] Int. Cl.$^5$ .................. B22D 25/00; C22C 21/06
[52] U.S. Cl. ........................... 148/3; 148/159; 148/417; 148/439; 420/534
[58] Field of Search ............ 148/439, 417, 2, 3, 148/12.7 A, 159; 420/534

[56] References Cited

U.S. PATENT DOCUMENTS 4,434,014 2/1984 Smith .................................. 148/3
4,934,442 6/1990 Futamura et al. ................... 148/3

FOREIGN PATENT DOCUMENTS 2085920A 5/1982 United Kingdom .

OTHER PUBLICATIONS

SAE Technical Paper Series No. 840123, of J. A. Eady and D. M. Smith Comalco Research Centre, International Congress & Exposition, Detroit, Mich., Feb. 27–Mar. 2, 1984.
SAE Technical Paper Series No. 860558, of R. A. Legge, D. M. Smith and G. Henkel, Comalco Research Centre, Australia, Copyright 1986 "Society of Automotive Engineers, Inc.".

Primary Examiner—Melvyn J. Andrews
Assistant Examiner—Robert R. Koehler
Attorney, Agent, or Firm—Marshall, O'Toole, Gerstein, Murray & Bicknell

[57] ABSTRACT

A squeeze formed aluminum-silicon cylinder liner for an internal combustion engine is produced from a melt consisting essentially of the following composition by weight: silicon 14% to 16%, copper 1.9% to 2.2%, nickel 1.0% to 1.4%, magnesium of 0.4% to 0.55%, iron 0.6% to 1.0%, manganese 0.3% to 0.6%, silicon modifier 0.02% to 0.1%, with the balance being aluminum and any unavoidable impurities, the as-formed article having an essentially eutectic microstructure containing not more than 10% of primary alpha-aluminum dendrites and being substantially free from intermetallic particles exceeding 10μ in diameter. The growth rate R of the solid phase during solidification is from 1,000 to 2,500 μ/s and the temperature gradient G at the solid/liquid interface, expressed in °C./cm is such that the ratio G/R is from 100 to 1,000° Cs/cm$^2$.

10 Claims, 1 Drawing Sheet

ALUMINUM-SILICON ALLOY ARTICLE AND METHOD FOR ITS PRODUCTION

This invention relates to an aluminium-silicon alloy article produced by a squeeze forming process and particularly, but not essentially, relates to a squeeze formed aluminium-silicon alloy cylinder liner for an internal combustion engine.

It is known that cylinder liners can be produced by squeeze forming aluminium alloys but, in order to provide adequate wear properties, the internal bores of such liners have hitherto required plating with a nickel-silicon carbide composite coating. Generally, such a coating process adds an unacceptable production cost to such liners.

It has been proposed in GB-A-2085920 of Comalco Limited to utilise a cast aluminium-silicon alloy in the production of various automotive components wherein the alloy has an essentially eutectic microstructure containing not more than 10% of primary alpha-aluminium dendrites and being substantially free from intermetallic particles exceeding $10\mu$ in diameter. Further discussion regarding the alloy, the subject of this patent specification, is to be found in SAE Technical Paper Series 840123 and 860558 wherein the alloy, identified by Comalco Limited as 3HA, is described as being castable by gravity, low pressure or high pressure casting methods.

It is to be understood from the above mentioned patent specification and papers that the properties of 3HA alloy are determined by the correct microstructure which in turn is produced by the specific alloy composition and its solidification parameters. For example, in the patent specification it is stated that strengthening of the matrix is enhanced by the presence of stable manganese and zirconium containing particles. It is also stated that titanium, because of its known grain refining characteristics, is added to improve castability and to improve the mechanical properties of the alloy.

We have discovered that articles of an aluminium-silicon alloy having similar desirable characteristics to those of the 3HA alloy can be produced from an alloy melt of a different composition to that of 3HA and with different solidification parameters. Hence it is an object of the present invention to provide a new or improved article of an aluminium-silicon alloy and the method for its production.

In accordance with the invention there is provided a squeeze formed aluminium-silicon alloy article produced from a melt consisting essentially of the following composition by weight:

| Silicon | 14% to 16% |
|---|---|
| Copper | 1.9% to 2.2% |
| Nickel | 1.0% to 1.4% |
| Magnesium | 0.4% to 0.55% |
| Iron | 0.6% to 1.0% |
| Manganese | 0.3% to 0.6% |
| Silicon Modifier | 0.02% to 0.1% | with the balance being aluminium and any unavoidable impurities, the as-formed article having an essentially eutectic microstructure containing not more than 10% of primary alpha-aluminium dendrites and being substantially free from intermetallic particles exceeding $10\mu$ in diameter.

The weight of silicon modifier in the melt may be within the range 0.02% to 0.08% and, preferably, the silicon modifier is strontium.

Also in accordance with the invention there is provided a method of producing the squeeze formed article as described above wherein, during the squeeze forming operation, the melt is solidified under conditions of sustained temperature and pressure such that the growth rate R of the solid phase during solidification is from 1,000 to 2,500 $\mu$/s and the temperature gradient G at the solid/liquid interface, expressed in $°C./cm$ is such that the ratio G/R is from 100 to 1,000 $°Cs/cm^2$.

The method may comprise the additional step of subjecting the as-formed article to a full heat treatment process being a solution treatment including heating and holding the article at a first temperature, water quenching the article and reheating and holding the article at a second temperature which is lower than said first temperature.

The squeeze formed aluminium-silicon alloy article referred to above conveniently comprises a cylinder liner for an internal combustion engine although squeeze formed articles produced in accordance with the invention may comprise other components where the wear resistant properties are of importance; thus, for example but without limitation, the article may comprise a reciprocable piston for an internal combustion engine or a compressor, or a brake disc or drum or brake cylinder for automotive application.

As will be known to those skilled in the art, the technique of squeeze forming essentially comprises introducing liquid metal into a first part of a mould, closing the mould under pressure so that the liquid metal fills the mould cavity without entrapping air, maintaining the metal under pressure whilst solidification takes place so as to ensure that any shrinkage cavities which may form are closed and filled, and then opening the mould and removing the formed article.

The squeeze forming process is thus different from gravity, low pressure or high pressure casting in that solidification of the melt takes place under conditions of sustained temperature and pressure. Typically, the pressure applied to the melt may be of the order of 70 MPa and may be sustained for a period of time of the order of 40 seconds. The solification parameters of the squeeze forming process are different to those obtaining in other known casting processes and hence, in accordance with the method of the invention, the desired microstructure can be obtained at a solidification growth rate R of the solid phase from 1,000 to 2,500 $\mu$/s whilst omitting zirconium and titanium from the composition. Specifically, titanium is not required as the desired degree of grain refinement is found to be present in the as-formed article as a direct consequence of the squeeze forming method of production.

Figure 2:
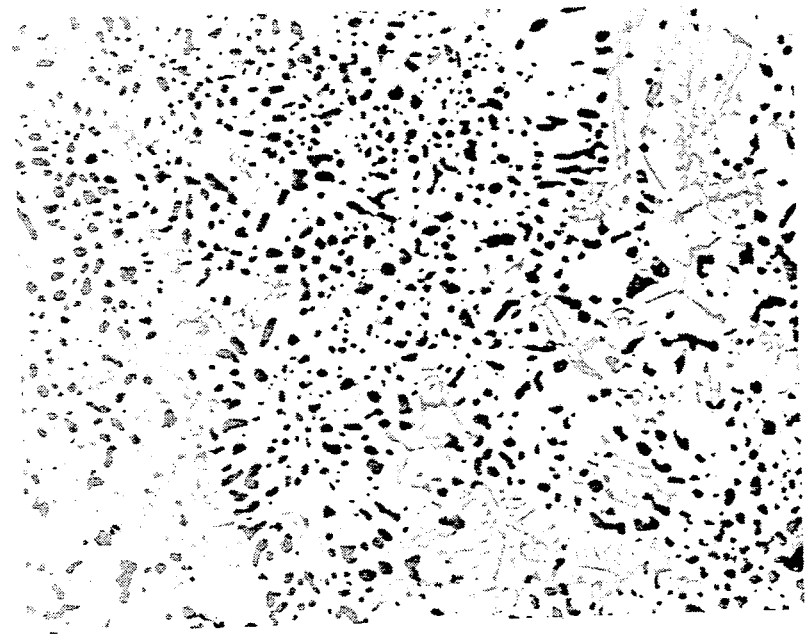

Cylinder liners for an internal combustion engine were produced in accordance with the invention and the microstructure of sections of one liner are shown in the accompanying figures wherein:

FIG. 1 is a photomicrograph to a magnification of $\times 400$ of an unetched section of the liner as formed, and FIG. 2 is a photomicrograph to a magnification of $\times 400$ of a corresponding unetched section of the liner after a full heat treatment process (T6).

By way of example, and for test purposes, cylinder liners for an external combustion engine were produced by squeeze forming aluminium-silicon alloy material to the following two compositions by weight:

| Example 1 | |
| --- | --- |
| Silicon | 14% to 16% |
| Copper | 1.9% to 2.2% |
| Nickel | 1.0% to 1.4% |
| Magnesium | 0.4% to 0.55% |
| Iron | 0.6% to 1.0% |
| Manganese | 0.3% to 0.6% |
| Strontium | 0.02% to 0.08% | with the balance being aluminium and incidental impurities.

| Example 2 | |
| --- | --- |
| Silicon | 14% to 16% |
| Copper | 1.9% to 2.2% |
| Nickel | 1.0% to 1.4% |
| Magnesium | 0.4% to 0.55% |
| Iron | 0.6% to 1.0% |
| Manganese | 0.3% to 0.6% |
| Strontium | 0.02% to 0.1% | with the balance being aluminium and incidental impurities.

During the squeeze forming of cylinder liners to both of the above compositions the growth rate R of the solid phase during solidification was from 1,000 to 2,500 $\mu$/s and the temperature gradient G at the solid/liquid interface, expressed in °C./cm, was such that the ratio G/R was from 100 to 1,000 °Cs/cm².

In the as-formed cylinder liner, the microstructure shown in the photomicrograph comprising FIG. 1 was found to be essentially eutectic containing not more than 10% of primary alpha-aluminium dendrites and being substantially free from intermetallic particles exceeding 10$\mu$ in diameter.

The as-formed liners were then given a full heat treatment process (T6) being a solution treatment of heating and holding the liners at approximately 480° C. to 530° C. for between 5 and 20 hours, quenching the liners into hot water and then artificially ageing them by reheating and holding at a temperature of around 140° C. to 250° C. for a time between two and 30 hours. The microstructure of such a heat treated liner is shown in the photomicrograph comprising FIG. 2 and after this full heat treatment the average mechanical properties were found to be:

| UTS | 350 to 380 MPa |
| --- | --- |
| Hardness (BHN) | 130 to 160 |
| 0.2% Compressive YS | 400 to 450 MPa. |

Further elevated temperature mechanical testing was carried out which yielded the following UTS values:

| 150° C. | 1 hour | 330 to 360 MPa |
| --- | --- | --- |
| | 1,000 hours | 300 to 320 MPa |
| 200° C. | 1 hour | 310 to 340 MPa |
| | 1,000 hours | 200 to 230 MPa |
| 250° C. | 1 hour | 220 to 240 MPa |
| | 1,000 hours | 100 to 150 MPa |

Under sliding wear conditions, the wear resistance properties of cylinder liners produced as described above were found to be excellent. Thus the article of the present invention enjoys the inherent advantages of a squeeze formed product in being produced to a high density without air entrapment in a relatively short production cycle time whilst also benefitting from the desirable properties of the essentially eutectic microstructure. Also, by utilisation of a squeeze forming process, the expensive alloying elements zirconium and titanium can be omitted.

We claim:

1. A squeeze formed aluminium-silicon alloy article produced from a melt consisting essentially of the following composition by weight:

| Silicon | 14% to 16% |
| --- | --- |
| Copper | 1.9% to 2.2% |
| Nickel | 1.0% to 1.4% |
| Magnesium | 0.4% to 0.55% |
| Iron | 0.6% to 1.0% |
| Manganese | 0.3% to 0.6% |
| Silicon Modifier | 0.02% to 0.1% | with the balance being aluminium and any unavoidable impurities, the as-formed article having an essentially eutectic microstructure containing not more than 10% of primary alpha-aluminium dendrites and being substantially free from intermetallic particles exceeding 10$\mu$ in diameter.

2. A squeeze formed article as claimed in claim 1 wherein the weight of silicon modifier in the melt is within the range 0.02% to 0.08%.

3. A squeeze formed article as claimed in either one of claims 1 or 2 wherein the silicon modifier is strontium.

4. A squeeze formed article according to claim 1 or 2 comprising a cylinder liner for an internal combustion engine.

5. A squeeze formed article according to claim 1 or 2 wherein the silicon modifier is strontium and the article comprises a cylinder liner for an internal combustion engine.

6. A method comprising:

producing a squeeze formed aluminium-silicon alloy article by forming a melt consisting essentially of the following composition by weight:

| Silicon | 14% to 16% |
| --- | --- |
| Copper | 1.9% to 2.2% |
| Nickel | 1.0% to 1.4% |
| Magnesium | 0.4% to 0.55% |
| Iron | 0.6% to 1.0% |
| Manganese | 0.3% to 0.6% |
| Silicon Modifier | 0.02% to 0.1% | with the balance being aluminium and any unavoidable impurities;

introducing the melt into a mould for the intended article;

applying squeezing pressure to the melt in the mould and while maintaining the melt under squeezing pressure permitting the melt to solidify under conditions of sustained temperature and pressure such that the growth rate R of the solid phase during solidification is from 1,000 to 2,500 $\mu$/s and the temperature gradient G at the solid/liquid interface, expressed in °C./cm is such that the ratio G/R is from 100 to 1,000 °Cs/cm² and the as-formed article has an essentially eutectic microstructure containing not more than 10% of primary alpha-aluminium dendrites and is substantially free from intermetallic particles exceeding 10) in diameter.

7. A method according to claim 6 comprising:
subjecting the as-formed article to a solution heat treatment process including heating and holding the article at a first temperature, water quenching the article and reheating and holding the article at a second temperature which is lower than said first temperature.

8. A method according to claim 6 or 7 in which the article is a cylinder liner for an internal combustion engine.

9. A method according to claim 6 or 7 in which the weight of silicon modifier in the melt is within the range of 0.02% to 0.08%.

10. A method according to claim 6 or 7 in which the silicon modifier is strontium.

* * * * *